United States Patent
Hudak, Jr.

(10) Patent No.: US 9,931,225 B2
(45) Date of Patent: Apr. 3, 2018

(54) ACETABULAR EXCISE DEVICE

(71) Applicant: Zimmer, Inc., Warsaw, IN (US)

(72) Inventor: John J. Hudak, Jr., Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 395 days.

(21) Appl. No.: 14/695,719

(22) Filed: Apr. 24, 2015

(65) Prior Publication Data

US 2015/0313722 A1 Nov. 5, 2015

Related U.S. Application Data

(60) Provisional application No. 61/988,564, filed on May 5, 2014.

(51) Int. Cl.
*A61F 2/46* (2006.01)

(52) U.S. Cl.
CPC .... *A61F 2/4609* (2013.01); *A61F 2002/4619* (2013.01); *A61F 2002/4623* (2013.01); *A61F 2002/4625* (2013.01); *A61F 2002/4681* (2013.01)

(58) Field of Classification Search
CPC ........ A61F 2/46; A61F 2/4603; A61F 2/4609; A61F 2002/4619; A61F 2002/4623; A61F 2002/4624; A61F 2002/4625; A61F 2002/4681
USPC ............ 606/99, 100; 81/177.2, 177.5, 177.7, 81/177.85
See application file for complete search history.

(56) References Cited

U.S. PATENT DOCUMENTS

| | | | | |
|---|---|---|---|---|
| 65,114 | A * | 5/1867 | Perkins | G05G 1/12 269/245 |
| 1,428,840 | A * | 9/1922 | Gates | B25B 13/466 279/24 |
| 1,457,570 | A * | 6/1923 | Guthard | B25G 1/005 439/817 |
| 1,683,384 | A * | 9/1928 | Durham, Jr. | B25B 23/0035 279/76 |
| 1,741,969 | A * | 12/1929 | Bellows | B25B 23/0035 403/317 |
| 3,738,768 | A * | 6/1973 | Kuhn | B25B 13/44 279/42 |
| 4,729,270 | A * | 3/1988 | Pritchard | B25B 13/00 81/177.5 |
| 6,260,452 | B1 * | 7/2001 | Yu | B25B 23/0021 81/177.2 |
| 7,331,261 | B2 * | 2/2008 | Blizniuk | B25B 23/0035 81/124.4 |
| 7,744,602 | B2 * | 6/2010 | Teeny | A61F 2/4609 606/100 |
| 7,749,227 | B2 * | 7/2010 | Lechot | A61B 17/1631 606/104 |

(Continued)

*Primary Examiner* — Eric S Gibson
(74) *Attorney, Agent, or Firm* — Schwegman Lundberg & Woessner, P.A.

(57) ABSTRACT

An acetabular cup excise device includes a cup excising portion, an elongated handle shaft extending along a longitudinal axis from the cup excising portion, and a positioning assembly operably coupled to the handle shaft. The positioning assembly is configured to allow rotation of a handle lever, about the longitudinal axis, to position the handle lever along at least a first radial axis perpendicular to the longitudinal axis and a second radial axis perpendicular to the longitudinal axis.

13 Claims, 7 Drawing Sheets

(56) References Cited

U.S. PATENT DOCUMENTS

| | | | | |
|---|---|---|---|---|
| 7,927,376 B2* | 4/2011 | Leisinger | A61F 2/34 | 606/91 |
| 8,475,460 B1* | 7/2013 | Roger | A61B 17/1666 | 606/80 |
| 8,834,471 B2* | 9/2014 | Roger | A61B 17/1664 | 606/80 |
| 2002/0116007 A1* | 8/2002 | Lewis | A61B 17/1666 | 606/99 |
| 2005/0252348 A1* | 11/2005 | Ting | B25B 13/06 | 81/177.5 |
| 2006/0200165 A1* | 9/2006 | Tulkis | A61B 17/1666 | 606/99 |
| 2007/0010825 A1* | 1/2007 | Leisinger | A61F 2/4637 | 606/99 |
| 2008/0195111 A1* | 8/2008 | Anderson | A61B 17/1666 | 606/90 |
| 2008/0275457 A1* | 11/2008 | Meek | A61F 2/38 | 606/99 |
| 2009/0216240 A1* | 8/2009 | Posdal | A61F 2/4609 | 606/99 |
| 2009/0281550 A1* | 11/2009 | Keller | A61F 2/4609 | 606/99 |
| 2010/0049327 A1* | 2/2010 | Isch | A61F 2/34 | 623/19.12 |
| 2010/0191246 A1* | 7/2010 | Howald | A61F 2/34 | 606/91 |
| 2010/0249796 A1* | 9/2010 | Nycz | A61F 2/4609 | 606/99 |
| 2012/0167726 A1* | 7/2012 | Cheng | B25B 23/0021 | 81/177.5 |
| 2012/0184964 A1* | 7/2012 | Hudak, Jr. | A61F 2/4609 | 606/91 |
| 2013/0331849 A1* | 12/2013 | Splieth | A61B 17/92 | 606/99 |
| 2015/0250614 A1* | 9/2015 | Davenport | A61F 2/4609 | 606/99 |
| 2015/0282856 A1* | 10/2015 | Haiat | A61B 17/92 | 606/100 |
| 2015/0313722 A1* | 11/2015 | Hudak, Jr. | A61F 2/4609 | 606/99 |
| 2016/0100957 A1* | 4/2016 | Lewis | A61F 2/4609 | 606/84 |

* cited by examiner

ACETABULAR EXCISE DEVICE

PRIORITY CLAIM

This patent application claims the benefit of priority, under 35 U.S.C. Section 119(e), to U.S. Application Ser. No. 61/988,564, entitled "ACETABULAR EXCISE DEVICE," filed on May 5, 2014, which is hereby incorporated by reference herein in its entirety.

TECHNICAL FIELD

This patent document pertains generally to a device and related methods for removing a prosthetic acetabular cup implanted into an acetabulum.

BACKGROUND

Prosthetic ball-and-socket hip joints can include a prosthetic femoral component and an acetabular component for replacing a worn or damaged femur and/or acetabulum. The hip replacement procedure typically includes a femoral head ostectomy in which a portion or all of the head and neck of the femur is removed. The prosthetic femoral component is implanted onto the remaining portion of the femur and positioned to correspond to the removed portions of the femur. Similarly, the acetabulum is often reshaped or hollowed out to receive a prosthetic acetabular cup for interfacing with the prosthetic femoral component. The acetabular cup can be made of stainless steel, titanium or other biocompatible materials. Certain acetabular cups can include a textured or porous exterior surface for facilitating ingrowth of bone into the exterior of the acetabular cup to fuse the acetabular cup to the acetabulum. Additionally, a liner of biocompatible material, such as ultra-high molecular weight polyethylene (UHMWPE), can be received within a hemispherical recess defined by the acetabular cup for receiving a femoral head portion of the prosthetic femoral component.

While the liner reduces the friction between the acetabular cup and the femoral component, the continual use of the prosthetic can cause wear damage or other damage to the liner of the acetabular cup or the acetabular cup itself, requiring revision surgery. Hip joint revision surgery to replace a damaged acetabular cup generally involves passing an osteotome blade of an osteotome between the acetabular cup and the acetabulum to sever ingrown bone to separate the acetabular cup from the acetabulum. Typically, the osteotome blade is positioned adjacent the edge of the acetabular cup and driven into bone adjacent the acetabular cup by striking a head of the osteotome opposite the blade with a mallet or similar device. The blade tip is aligned with the edge of the acetabular cup and driven between the exterior surface of the acetabular cup and acetabulum to sever the ingrown bone. A plurality of cuts can be made by pivoting the blade and repeating the cut. The plurality of driven cuts required for the conventional osteotome slows the removal process and increases discomfort for the patient. A similar challenge is that portions of the patient's body such as the patient's legs or torso can limit the possible orientations at which the head of the osteotome can be positioned for efficient striking to drive the blade. In addition, the surgeon is often required to awkwardly reach or move about the patient's body to position head and drive the blade.

OVERVIEW

The present inventors have recognized, among other things, that improvements can be made to acetabular excise devices and related surgical procedures that can allow for an easier, more efficient removal of an acetabular cup from an acetabulum. An acetabular excise devices can have a handle extending from the osteotome blade can be required to apply leverage to the osteotome blade when working the blade between the acetabular cup and acetabulum. However, the necessary length of the handle shaft of acetabular cup excise instrument during the cutting process can prevent applying effective leverage to the osteotome blade or cause the handle shaft to strike the patient's body or other obstructions. The inability to effectively position the excise instruments in positions for efficient driving of the blade due to obstructions such as the patient's limbs or torsos substantially increases the time required to remove the acetabular cup increasing discomfort for the patient and can slow recovery time. In addition, in certain situations applying leverage along a different axis or plane after placing or driving the osteotome blade into the ingrown bone can be advantageous in working the blade through the ingrown bone.

According to the present disclosure, an acetabular excise device for removing an acetabular cup can include a cup excising portion, a handle shaft, a positioning assembly and a handle lever. The handle shaft can extend from the cup excising portion along a longitudinal axis. The positioning assembly can be operably coupled to the handle shaft and can be configured to rotate the handle lever relative to the handle shaft to reposition the handle lever along a plurality of radial axes perpendicular to the longitudinal axis to, for example, improve leverage or avoid obstructions. The positioning assembly can also be configured to slide the handle lever axially for improving leverage and/or avoiding obstructions. The ability to reposition the handle lever can help avoid injury to the patient and shorten surgical time by providing improved leverage or clearance, thereby extending cuts that would otherwise require the blade to be removed from the acetabular cup and reinserted in a new position.

In an example, during a surgical procedure, the blade can be placed at an initial position adjacent the acetabular cup for cutting bone in grown into the acetabular cup. The handle can be initially positioned along an initial radial axis for positioning the cup excising portion without snagging the handle or blocking the operating room personnel. In at least one example, the handle shaft can be disengaged from the positioning assembly and the handle lever, if necessary, to avoid obstructions when positioning the cup excising portion. The handle can then be manipulated to apply torque to the cup excising portion with the handle at the initial position or the handle can be repositioned along a different radial axis to apply torque to the cup excising portion from a different angle depending on the needs of the procedure. In at least one example, the handle can be removed and the handle shaft can be manually maneuvered without the handle lever.

According to the present disclosure, an acetabular excise device can include a cup excising portion, a handle shaft, a positioning element and a handle lever. The handle shaft can extend from the cup excising portion along a longitudinal axis. The positioning element can be operably coupled to the handle shaft and can include a rotating element defining a through-hole for receiving the handle lever. The rotating element can be configured to rotate around the longitudinal axis to rotate the handle lever between a first radial axis perpendicular to the longitudinal axis and a second radial axis perpendicular to the longitudinal axis. According to the present disclosure, the positioning element can include a rotating locking element affixed to the handle shaft and configured to selectively engage the rotating element. In this configuration, the rotating locking element can selectively engage the rotating element to fix the handle lever at a particular radial axis. Similarly, the rotating locking element can be disengaged to permit the rotating element to allow rotational repositioning of handle lever. In an example, the positioning element can include a ratcheting assembly for limiting rotation of the handle lever in a single rotational direction.

According to the present disclosure, the handle lever can be slidably received within the through-hole such that the handle lever can slide axially along a radial axis perpendicular to the longitudinal axis. In this configuration, the positioning assembly can include a sliding-locking element that selectively engages the handle lever. The sliding-locking element can selectively engage the handle lever and fix the handle lever at a particular axial position.

According to the present disclosure, a method for excising an acetabular cup can include providing an acetabular excise device that includes a cup excising portion, a handle shaft, a positioning element and a handle lever, wherein the handle shaft extends from the cup excising portion along a longitudinal axis. The method can further include engaging the acetabular cup with the cup excising portion, wherein the cup excising portion includes an osteotome blade insertable along an edge of the acetabular cup. The method can further include rotating the handle lever between a first radial axis perpendicular to the longitudinal axis and a second radial axis perpendicular to the longitudinal axis. The method can further include sliding the handle lever axially between a first axial position and a second axial position. Finally, the method can further include manually operating the handle lever to move the osteotome blade in an orbital fashion about the acetabular cup.

These and other examples and features of the present acetabular excise device will be set forth in part in the following detailed description. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, like numerals can be used to describe similar elements throughout the several views. The drawings illustrate generally, by way of example, but not by way of limitation, various embodiments discussed in the present document.

DETAILED DESCRIPTION

Figure 1:
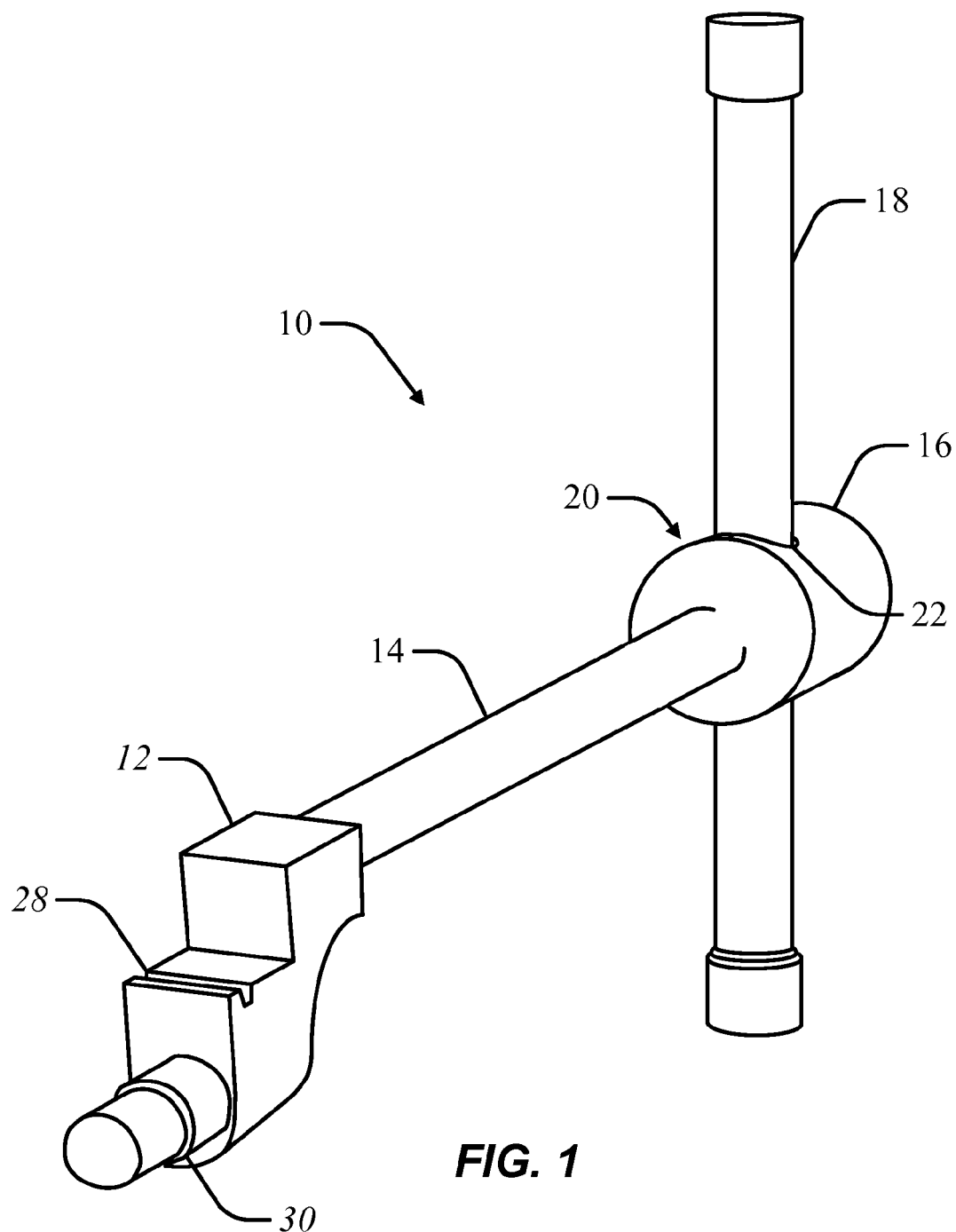
FIG. 1 is a perspective view of an acetabular cup excise device according to at least one example of the present subject matter.
Figure 2:
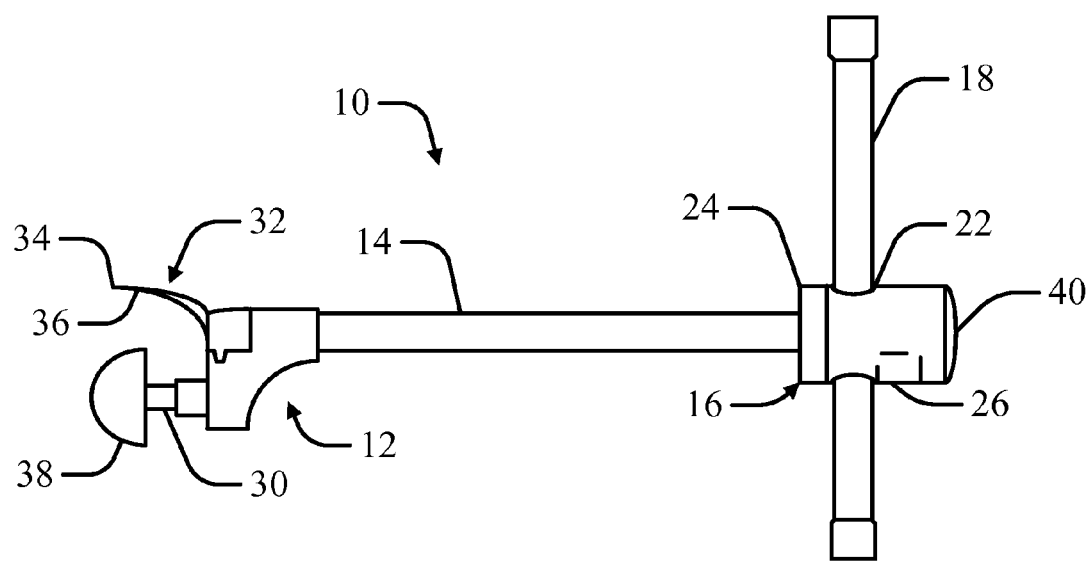
FIG. 2 is a side view of an acetabular cup excise device according to at least one example of the present subject matter.

As depicted in FIGS. 1-2, an acetabular cup excise device 10, according to at least one example, can include a cup excising portion 12, an elongated handle shaft 14, a positioning assembly 16 and a handle lever 18. The elongated handle shaft 14 can extend from the cup excising portion 12 along a longitudinal axis. The handle shaft 14 can be manipulated to rotate and reorient the cup excising portion 12. The positioning assembly 16 can be positioned along the elongated handle shaft 14 and configured to position the handle lever 18 along a radial axis generally perpendicular to the longitudinal axis. The handle lever 18 can be manipulated to apply leverage to the cup excising portion 12. In at least one example, the handle lever 18 can be repositioned by rotating the positioning assembly 16 to position the handle lever 18 along a second radial axis. The handle lever 18 can also be slid axially to improve the maneuverability of the acetabular cup excise device 10 and changing the direction and amount of leverage applied to the cup excising portion 12.

The positioning assembly 16 can include a rotating element 20 defining a through-hole 22 for slidably receiving the handle lever 18. The through-hole 22 can be oriented transverse to the longitudinal axis of the elongated handle lever 18. The rotating element 20 can be rotatable about the longitudinal axis such that the handle lever 18 can be positionable along any one of a plurality of radial axes generally perpendicular to the longitudinal axis including those depicted in FIGS. 5-6. In this configuration, the handle lever 18 can be positioned radially to provide additional clearance to manipulate the handle lever 18 or prevent contacting of the handle shaft 14 or handle lever 18 with the patient during manipulating of the handle lever 18. The radial repositioning of the handle lever 18 allows changing of the direction along which leverage is applied to the cup excising portion 12. In at least one example, the rotating element 20 can be configured to rotate between a plurality of pre-defined positions.

Figure 5:
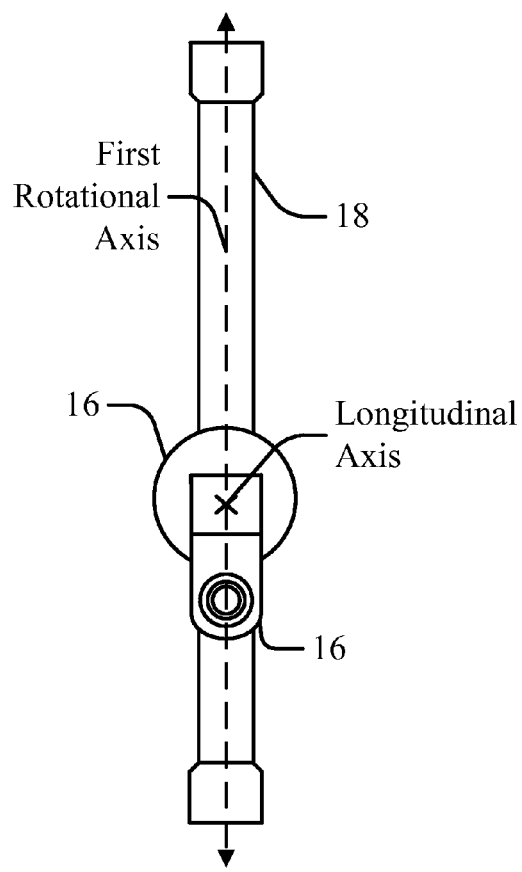
FIG. 5 is a front view of an acetabular cup excise device, according to at least one example of the present subject matter, having a handle lever positioned in a first rotational position.
Figure 6:
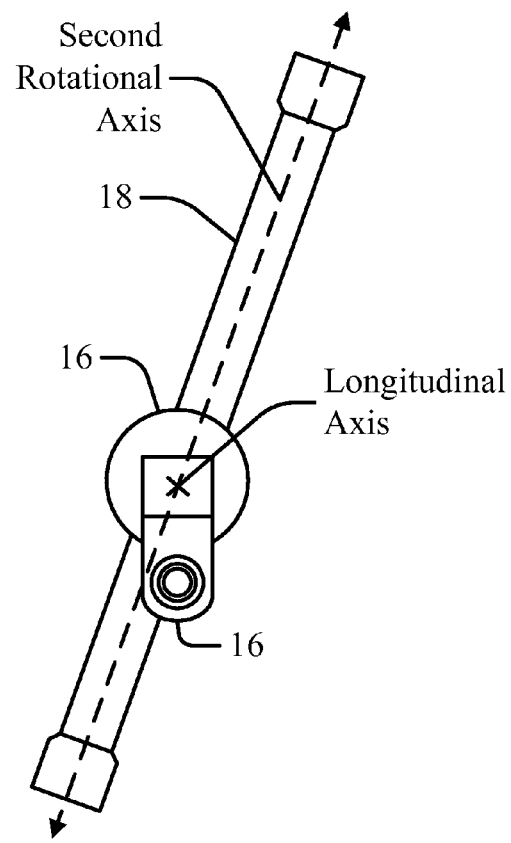
FIG. 6 is a front view of an acetabular cup excise device, according to at least one example of the present subject matter, having a handle lever positioned in a second rotational position.

As illustrated in FIG. 5, the handle lever 18 can be positioned along a first radial axis perpendicular to the longitudinal axis. The handle lever 18 can be rotated about the positioning apparatus 16 to position the handle lever 18 along a second radial axis perpendicular to the longitudinal axis as illustrated in FIG. 6.

Figure 7:
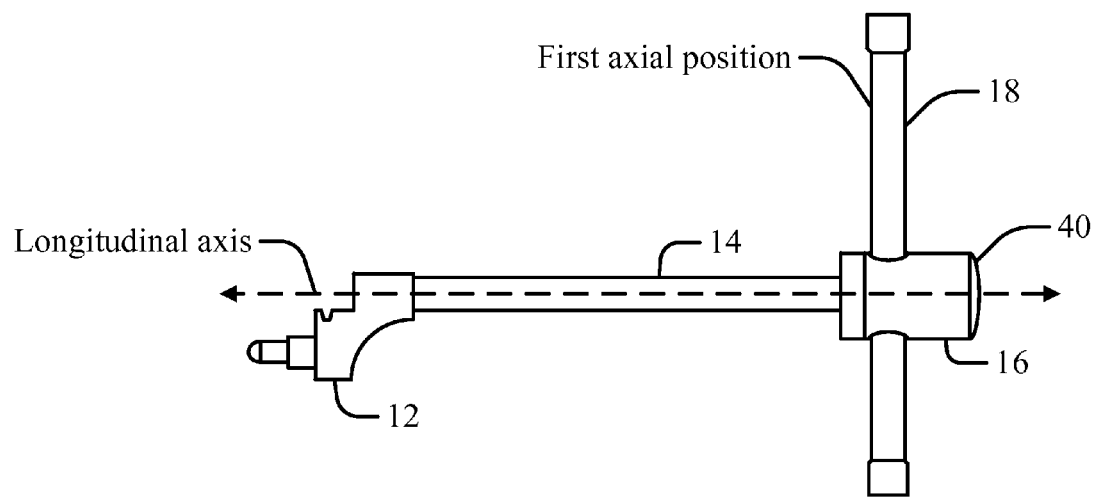
FIG. 7 is a side view of an acetabular cup excise device, according to at least one example of the present subject matter, having a handle lever positioned in a first axial position.
Figure 8:
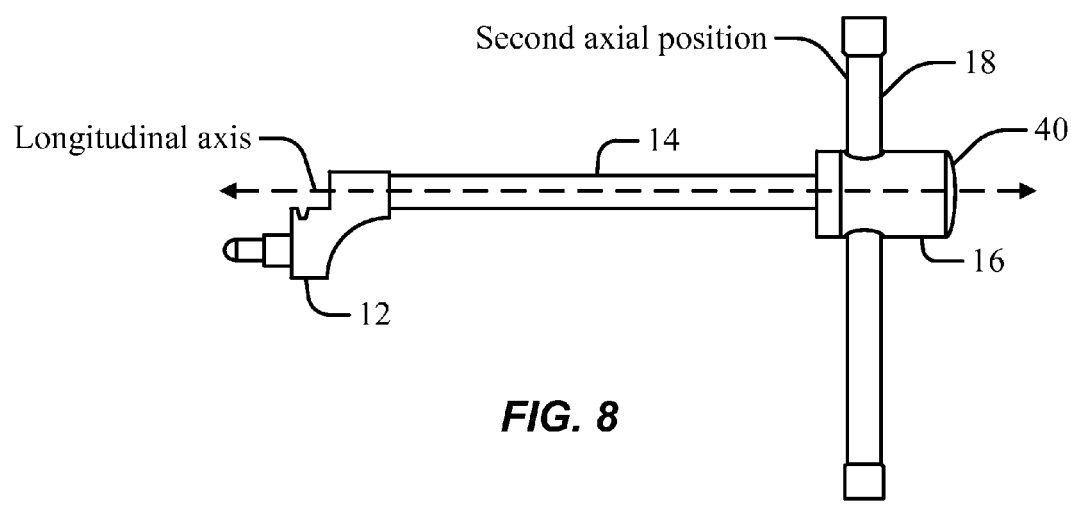
FIG. 8 is a side view of an acetabular cup excise device, according to at least one example of the present subject matter, having a handle lever positioned in a second axial position.

As illustrated in FIGS. 7-8, the handle lever 18 can be moved axially within the through-hole 22 to position the handle lever 18 at a plurality of axial positions including those depicted in FIGS. 7-8. In this configuration, the handle lever 18 can be positioned axially to allow the operator more available hand positions or orientations relative to the cup excising portion 12 to provide improved control or torque when maneuvering or manipulating the cup excising portion 12.

In an example, the handle lever 18 can be positioned in a first axial position as illustrated in FIG. 7. The handle lever 18 can be slid within the through-hole 22 to position the handle lever 18 as illustrated in FIG. 8. The through-hole 22 can be perpendicular to the longitudinal axis such that sliding the handle lever 18 axially slides the handle lever 18 along a radial axis perpendicular to the longitudinal axis.

As illustrated in FIG. 2, in an example, the positioning assembly 16 can further include a rotational locking element 24 affixed to the handle shaft 14 and selectively engagable to the rotating element 20 to limit rotation of the rotating element 20 relative to the handle shaft 14. In at least one example, the rotational locking element 24 can include a spring biased detent engagable with a corresponding notch in the rotating element 20 to prevent rotation of the rotating element 20. In another example, the rotational locking element 24 can include a ratcheting assembly including a spring biased tab that can releasably engage a plurality of shaped notches that are oriented to permit rotation of the rotating element 20 in only a first direction. In at least one example, the ratcheting assembly can include a second plurality of oppositely shaped notches and a selector assembly that can be operated to switch the permitted rotation direction of the rotating element to a second direction opposite the first direction. In at least one example, the rotational locking element 24 can include a plurality of notches that can be selectively engaged to a plurality of corresponding notches on the rotating element 20 to prevent rotation of the rotating element 20 relative to the rotational locking element 24. In this configuration, the rotational locking element 24 can include, but is not limited to, a set screw, a biasing spring or other element for biasing the notches of the rotating element 20 and the rotational locking element 24 into engagement.

As further illustrated in FIG. 2, in an example, the positioning assembly 16 can include a slide locking element 26 selectively engagable to the handle lever 18 to prevent axial movement of the handle lever 18 through the through-hole 22. In at least one example, the slide locking element 26 can include a spring biased tab or detent engagable to a plurality of notches spaced along the handle lever 18. Similarly, the slide locking element 26 can include a set screw that can be extended into the plurality of notches spaced along the handle lever 18. In at least one example, the slide locking element 26 can include a friction sleeve that can be tightened about the handle lever 18 to prevent axial movement of the handle lever 18.

Figure 3:
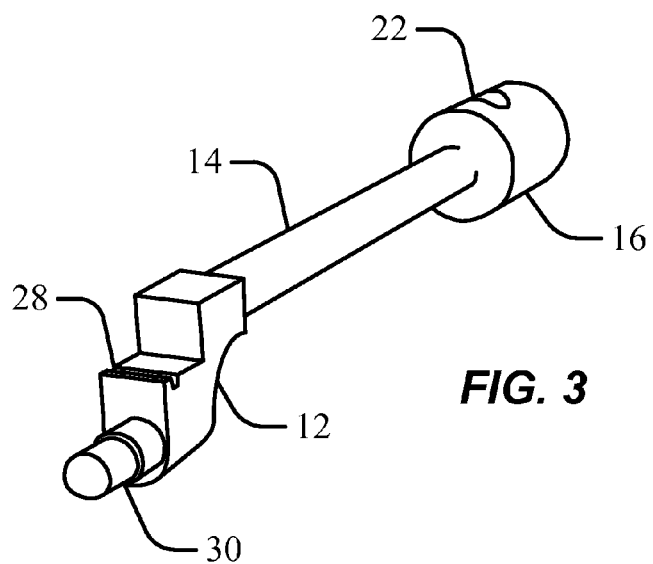
FIG. 3 is a perspective view of a cup excising portion, an elongated handle shaft and a positioning assembly according to at least one example of the present subject matter.

In an example, as illustrated in FIGS. 1 and 3, the cup excising portion 12 can include an osteotome blade mount 28 and a pivot element 30. The blade mount 28 can be configured to receive an interchangeable osteotome blade 32, as depicted in FIG. 2. Each osteotome blade 32 can include a blade tip 34 and a blade body having a predetermined curvature 36. In at least one example, the pivot element 30 can be aligned with the longitudinal axis while the blade mount 28 can be offset from the longitudinal axis. In operation, the pivot element 30 can be inserted into the recess of an acetabular cup, wherein the offset distance of the blade mount 28 positions the blade tip 34 of the osteotome blade 32 proximate the edge of the acetabular cup. The pivot element 30 can center the elongated shaft 14 relative to the acetabular cup such that the blade tip 34 is positioned proximate the edge of the acetabular cup as the osteotome blade 32 is moved about the acetabular cup and driven between the acetabular cup and the corresponding bone. In an example, as illustrated in FIG. 2, the pivot element 30 can be configured to be fitted with a ball head 38 corresponding to the curvature of the acetabular cup to be removed. In an example, the osteotome blade 32 can be interchanged with a different osteotome blade 32 have a different curvature to correspond to a different size acetabular cup.

Figure 4:
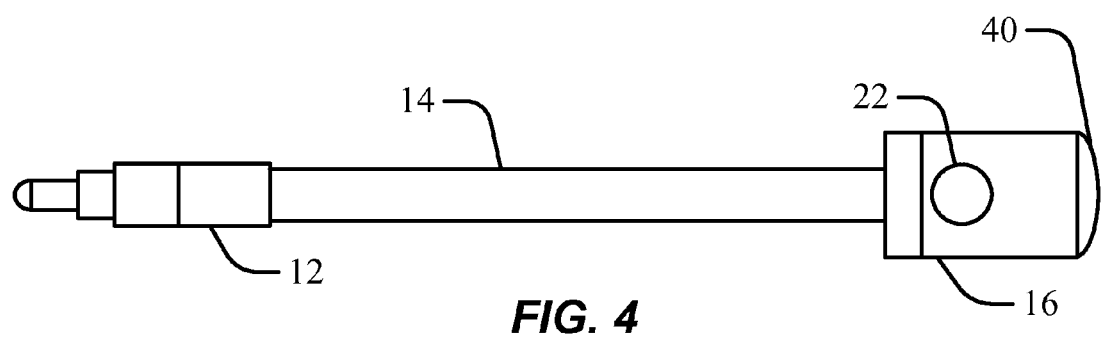
FIG. 4 is a top view of a cup excising portion, an elongated handle shaft and a positioning assembly according to at least one example of the present subject matter.

As further illustrated in FIGS. 2 and 4, in an example, the positioning assembly 16 can include a strike plate 40. During an acetabular cup removal procedure, the strike plate 40 can be tapped or impacted by a hammer, mallet or other tool to aid in the working of the osteotome blade 32. In an example, the strike plate 40 can be adapted to translate impacts from the tool through the strike plate 40 into the handle shaft 14. The handle shaft 14 can be configured to transmit the impact from the strike plate 40 to the cup excising portion 12. In this configuration, the strike plate 40 can be struck in line with the handle shaft 14 to drive the blade 32 along an axis parallel to the axis of the handle shaft 14 or force the ball head 38 into the acetabular cup. Similarly, the strike plate 40 can be struck along an axis transverse to the axis of the handle shaft 14, which can cause the offset blade 32 to pivot about the ball head 38.

Figure 9:
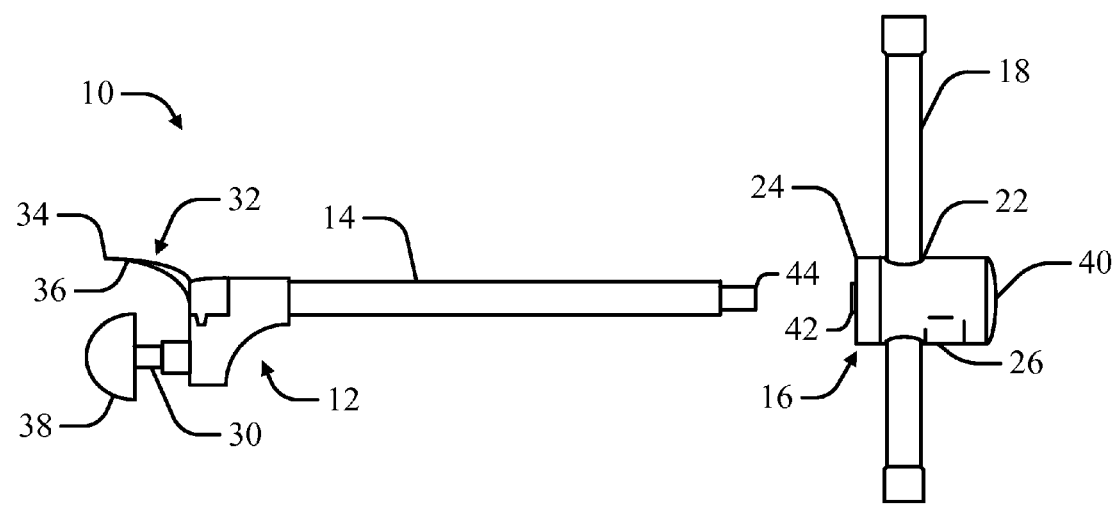
FIG. 9 is a side view of an acetabular excised device, according to at least one example of the present subject matter, having a positioning assembly that can be disconnected from the handle shaft.

As illustrated in FIG. 9, in an example, the positioning assembly 16 can comprise an engagement feature 42 for interfacing with a corresponding connector feature 44 on the handle shaft 14. In this configuration, the positioning assembly 16 can be releasably coupled to the handle shaft 14 for positioning and leveraging the cup excising portion 12. As depicted in FIG. 9, in at least one example, the connector feature 44 can include a protruding portion received within a notch defined by the engagement feature 42. In this configuration, the protruding portion strengthens the connection between the handle shaft 14 and the position assembly 16 avoiding inadvertent disengagement when applying torque to the lever handle 18. In at least one example, the engagement feature 42 can comprise at least one feature that can be spring biased, flexed or otherwise moved to engage a corresponding notch or other feature on the connector feature 44. In at least one example, the engagement feature 42 can include a threaded feature engagable to a corresponding threaded feature on the connector feature 44. In at least one example, the engagement feature 42 can include a magnetic feature or other non-mechanically engaging feature that can engage to a corresponding feature on the connector feature 44. As discussed above, the various features can be interchangeably positioned on the engagement feature 42 and the connector feature 44.

In operation, the handle shaft 14 can initially position the cup excising portion 12 with the positioning assembly 16 and handle lever 18 removed, thereby reducing structure that could interfere with the patient's body or other objects. In at least one example, the engagement feature 42 can then be coupled to the connector feature 44 to secure the positioning assembly 16 and handle lever 18 to the handle shaft 14 and the cup excising portion 12 for leveraging and maneuvering the cup excising portion 12. In at least one example, the engagement feature 42 and the connector feature 44 can be engaged such that the positioning assembly 16 cannot be rotated relative to the handle shaft 14 engagement feature. In this configuration, the rotational locking element 24 can be operated to rotate the handle lever 18 relative to the handle shaft 14. In at least one example, the engagement feature 42 and the connector feature 44 can be engaged such that the positioning assembly 16 can be selectively rotated relative to the handle shaft 14.

Figure 10:
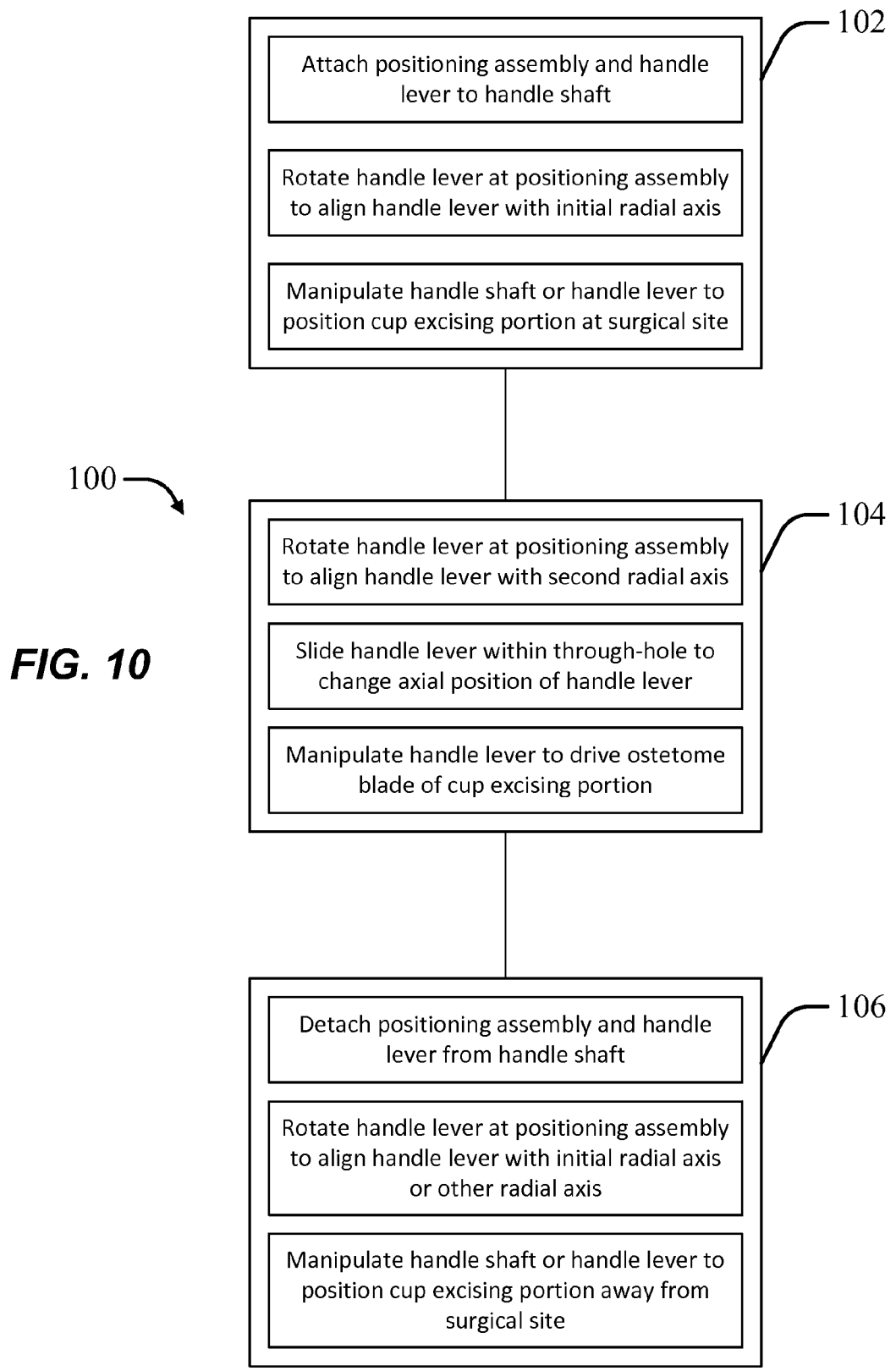
FIG. 10 is a schematic diagram illustrating a method of operating an acetabular excised device, according to at least one example of the present subject matter.

As depicted in FIG. 10, a method 100 for operating an acetabular cup excise device 10, according to at least one example, can include an initial positioning phase 102, an operating phase 104 and a removal phase 106.

During the initial positioning phase 102, the handle shaft 14 or the handle lever 18 can be manipulated to align the blade tip 34 of the osteotome blade 32 adjacent the edge of the acetabular cup. The handle lever 18 can be optionally rotated about the positioning assembly 16 to align the handle lever 18 with a radial axis that avoids obstructions or to improve the handling characteristics of the acetabular cup excise device 10. In at least one example, the handle shaft 14 can be manipulated to position the cup excising portion 12 with the positioning assembly 16 and the handle lever 18 detached from the handle shaft 14 to further avoid obstructions or to improve the handling characteristics of the acetabular cup excise device 10. After positioning of the cup excising portion 12 by manipulating the handle shaft 14, the positioning assembly 16 and the handle lever 18 can be attached to the handle shaft 14 for driving of the osteotome blade 32 or further positioning of the cup excising portion 12.

During the operating phase 104, the handle lever 18 can be manipulated to drive the blade tip 34 along the exterior of the acetabular cup to sever ingrown bone. The handle lever 18 can be optionally rotated about the positioning assembly 16 to align the handle lever 18 with a second radial axis to improve leverage when driving the blade tip 34. In at least one example, the handle lever 18 can be optionally slid within the through-hole 22 to change the axial position of the handle lever 18. In certain axial positions, the handle lever 18 can be gripped on either side of the positioning assembly 16 for improved control or manipulating of the cup excising portion 12. In at least one example, the handle lever 18 can be manipulated to drive the blade tip 34 and repositioned axially or radially to improve leverage on the handle lever 18 to withdraw the blade tip 34 for additional cuts.

During the removal phase 104, the handle lever 18 can be manipulated to remove the cup excising portion 12 from the surgical site. The handle lever 18 can be optionally rotated about the positioning assembly 16 to align the handle lever 18 with the initial radial axis or other radial axis that avoids obstructions or to improve the handling characteristics of the acetabular cup excise device 10 when removing the cup excising portion 12. In at least one example, the handle shaft 14 can be manipulated to position the cup excising portion 12 with the positioning assembly 16 and the handle lever 18 detached from the handle shaft 14 to further avoid obstructions or to improve the handling characteristics of the acetabular cup excise device 10.

The handle lever 18 can be repositioned radial and axially a plurality of times in each of the initial positioning phase 102, the operating phase 104 and the removal phase 106 depending on the needs of the particular surgical procedure. The size and condition of the patient, the size of the operating room, equipment in the operating room, the number of operating room personnel, the size and strength of the operating room personnel operating the acetabular excise device 10 and other factors can all affect the positioning and repositioning of the handle lever 18. Similarly, the positioning assembly 16 and the handle lever 18 can be detached and reattached depending on the needs of the particular surgical procedure. The handle shaft 14 can be manipulated to maneuver the cup excising portion 12 without the positioning assembly 16 and the handle lever 18 attached.

VARIOUS NOTES & EXAMPLES

Example 1 can include subject matter such as an acetabular cup excised device, such as can include a cup excising portion; an elongated handle shaft and a positioning assembly. The elongated handle shaft can extend along a longitudinal axis from the cup excising portion. The positioning assembly can be operably coupled to the handle shaft. The positioning assembly can have a rotating element that can be operably engaged to a handle lever. The rotating element can be rotated to position a handle lever along at least a first radial axis perpendicular to the longitudinal axis and a second radial axis perpendicular to the longitudinal axis.

Example 2 can include, or can optionally be combined with the subject matter of Example 1, wherein the rotating element optionally defines a through-hole for receiving the handle lever. The through-hole can extend in a direction transverse to the longitudinal axis.

Example 3 can include, or can optionally be combined with the subject matter of one or any combination of Examples 1 or 2 wherein the positioning assembly can optionally include a rotational locking element engagable with the rotating element and configured to lock the rotating element and the handle lever along a selected radial axis.

Example 4 can include, or can optionally be combined with the subject matter of Example 3, wherein the rotational locking element can selectively engages the rotating element to prevent rotation of the rotating element in a first direction.

Example 5 can include, or can optionally be combined with the subject matter of Example 4, wherein the rotational locking element can selectively engage the rotating element to prevent rotation of the rotating element in a second rotational direction. The second rotational direction being opposite to the first rotational direction.

Example 6 can include, or can optionally be combined with the subject matter of one or any combination of Examples 1 to 5 wherein the handle lever can be slidably received within the through-hole such that the handle lever is slidable within the through-hole between at least a first axial position and a second axial position.

Example 7 can include, or can optionally be combined with the subject matter of Example 6, wherein the positioning assembly can optionally further comprise a slide locking element. The slide locking element can selectively engage the handle lever to lock the handle lever in a desired axial position.

Example 8 can include, or can optionally be combined with the subject matter of one or any combination of Examples 1 to 7 wherein the handle lever can optionally include a connector feature. The positioning assembly can also include an engagement feature. The engagement feature of the positioning assembly can be engaged with the connector feature of the handle shaft to releasably connect the handle shaft to the positioning assembly.

Example 9 can include, or can optionally be combined with the subject matter of one or any combination of Examples 1 to 8 wherein the positioning assembly optionally further includes a strike plate. Impaction forces applied to the strike plate can be translated to the handle shaft and the cup excising portion along the longitudinal axis.

Example 10 can include subject matter such as a method of excising an acetabular cup fused to an acetabulum with an acetabular cup excise device, such as can include a method step of providing or obtaining an osteotome blade of a cup excising portion positionable adjacent to an acetabular cup. An elongated handle shaft can extend from the cup excising portion along a longitudinal axis. A positioning assembly can be configured to receive a handle lever is operably coupled to the elongated handle shaft. The method can include the method steps of positioning the handle lever along a first radial axis perpendicular to the longitudinal axis and rotating handle lever at the positioning assembly about the longitudinal axis to position the handle lever along a second radial axis.

Example 11 can include, or can optionally be combined with the subject matter of Example 10, wherein the method can further include the steps of positioning the osteotome blade adjacent to an acetabular cup; manipulating the handle lever to apply torque to the cup excising portion; and rotating the positioning assembly to position the handle lever along a selected radial axis perpendicular to the longitudinal axis; and manipulating the rotated handle lever to apply torque to the cup excising portion.

Example 12 can include, or can optionally be combined with the subject matter of one or any combination of Examples 10 or 11, wherein the method can optionally further include locking the positioning assembly to fix the handle lever at a set radial axis.

Example 13 can include, or can optionally be combined with the subject matter of one or any combination of Examples 10 to 12, wherein the method can optionally further include sliding the handle lever within a through-hole defined by positioning assembly relative to the positioning assembly between a first axial position and a second axial position.

Example 14 can include, or can optionally be combined with the subject matter of one or any combination of Examples 10 to 13, wherein the method can optionally further include positioning the osteotome blade adjacent an acetabular cup; positioning the handle lever in a selected axial position; and manipulating the handle lever to maneuver the blade between the acetabular cup and the acetabulum.

Example 15 can include, or can optionally be combined with the subject matter of Example 14, wherein the method can optionally further include locking the handle lever to prevent axial movement of the handle lever.

Example 16 can include, or can optionally be combined with the subject matter of one or any combination of Examples 10 to 15, wherein the method can optionally further include engaging a engagement feature of the positioning assembly with a connector feature of the handle shaft to releasably connect the handle shaft to the positioning assembly.

Example 17 can include, or can optionally be combined with the subject matter of Example 16, wherein the method can optionally further include disengaging the engagement feature of the positioning assembly from the connector feature of the handle shaft; and manipulating the handle shaft to maneuver the osteotome blade between the acetabular cup and the acetabulum.

Example 18 can include, or can optionally be combined with the subject matter of one or any combination of Examples 10 to 17, wherein the method can optionally further include striking a strike plate operably coupled to the positioning assembly. The impacts to the strike plate can be translated by the positioning assembly and the handle shaft to the cup excising portion along the longitudinal axis.

Each of these non-limiting examples can stand on its own, or can be combined in any permutation or combination with any one or more of the other examples.

The above Detailed Description includes references to the accompanying drawings, which form a part of the Detailed Description. The drawings show, by way of illustration, specific embodiments in which the present resection shift block and method can be practiced. These embodiments are also referred to herein as "examples." While the Detailed Description focuses on use of the resection shift block and method with a knee arthroplasty procedure, similar embodiments for use with other orthopedic non-knee joint procedures are also envisioned.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. The Abstract is provided to allow the reader to quickly ascertain the nature of the technical disclosure. It is submitted with the understanding that it will not be used to interpret or limit the scope or meaning of the claims.

What is claimed is:

1. An acetabular cup excise device, comprising:
   a cup excising portion having an osteotome blade and a pivot element;
   an elongated handle shaft extending along a longitudinal axis from the cup excising portion, wherein the osteotome blade is mounted in line with the longitudinal axis and the pivot element is radially offset from the longitudinal axis; and
   a positioning assembly operably coupled to the handle shaft, the positioning assembly having a rotating element operably engaged to a handle lever;
   wherein the rotating element is rotatable about the longitudinal axis to position the handle lever along at least a first radial axis perpendicular to the longitudinal axis for leveraging the osteotome blade about the pivot element about a first arc and a second radial axis perpendicular to the longitudinal axis for leveraging the osteotome blade about the pivot element about a second arc different from the first arc.

2. The acetabular cup excise device of claim 1, wherein the rotating element defines a through-hole for receiving the handle lever, the through-hole extending in a direction transverse to the longitudinal axis.

3. The acetabular cup excise device of claim 2, wherein the handle lever is slidably received within the through-hole such that the handle lever is slidable within the through-hole between at least a first axial position and a second axial position.

4. The acetabular cup excise device of claim 3, the positioning assembly further comprising:
a slide locking element selectively engagable to the handle lever to lock the handle lever in a desired axial position.

5. The acetabular cup excise device of claim 1, the positioning assembly further comprising:
a rotational locking element engagable with the rotating element and configured to lock the rotating element and the handle lever along a selected radial axis.

6. The acetabular cup excise device of claim 5, wherein the rotational locking element further selectively engages the rotating element to prevent rotation of the rotating element in a first direction.

7. The acetabular cup excise device of claim 6, wherein the rotational locking element selectively engages the rotating element to prevent rotation of the rotating element in a second rotational direction, the second rotational direction being opposite to the first rotational direction.

8. The acetabular cup excise device of claim 1, wherein the handle shaft further includes a connector feature and the positioning assembly includes an engagement feature;
wherein the engagement feature of the positioning assembly is engagable with the connector feature of the handle shaft to releasably connect the handle shaft to the positioning assembly.

9. The acetabular cup excise device of claim 1, wherein the positioning assembly further comprises a strike plate;
wherein impaction forces applied to the strike plate are translated to the handle shaft and the cup excising portion along the longitudinal axis.

10. The acetabular cup excise device of claim 1, wherein the osteotome blade and the pivot element are positioned within a plane.

11. The acetabular cup excise device of claim 10, wherein the osteotome blade is curved within the plane toward the pivot element.

12. The acetabular cup excise device of claim 11, wherein the first radial axis is within the plane and the second radial axis is transverse to the plane.

13. The acetabular cup excise device of claim 12, wherein the first arc is within the plane when the handle lever is positioned at the first radial axis and leveraged toward to the pivot element.

* * * * *